United States Patent [19]

Meakins et al.

[11] Patent Number: 5,079,386

[45] Date of Patent: Jan. 7, 1992

[54] PROCESS FOR THE PREPARATION OF ALKYL SUBSTITUTED TETRALINS AND INDANES

[75] Inventors: Stephen E. Meakins; Keith R. Motion; Christopher P. Newman, all of Kent, England

[73] Assignee: Unilever Patent Holdings B.V., Rotterdam, Netherlands

[21] Appl. No.: 598,886

[22] Filed: Oct. 19, 1990

Related U.S. Application Data

[63] Continuation-in-part of Ser. No. 508,716, Apr. 16, 1990, abandoned.

[30] Foreign Application Priority Data

Apr. 14, 1989 [EP] European Pat. Off. ............ 89200943

[51] Int. Cl.$^5$ .............................................. C07C 15/00
[52] U.S. Cl. .................................. 585/409; 585/408; 568/425; 568/626; 568/715
[58] Field of Search ................ 585/408, 409; 568/425, 568/626, 715

[56] References Cited

U.S. PATENT DOCUMENTS

| | | | |
|---|---|---|---|
| 2,519,576 | 8/1950 | Ipatieff et al. | 583/409 |
| 2,587,577 | 3/1952 | Iputieff et al. | 585/409 |
| 2,752,404 | 6/1956 | Polak | 585/409 |
| 2,857,433 | 10/1958 | Buson et al. | 585/409 |
| 3,210,433 | 10/1965 | Chibnik | 260/668 |
| 3,246,044 | 4/1966 | Wood et al. | 585/409 |
| 4,740,646 | 4/1988 | Henker et al. | 585/409 |

OTHER PUBLICATIONS

Journal of Organic Chemistry, vol. 45, No. 10 (May 19, 1980) pp. 2006–2008.
Ross et al., "A Cyclizations Yielding Bicyclic Compounds ... Derivatives", pp. 816–822, 1964.
Wood, T. F., Chemistry of the Aromatic Musks, pp. 1–37.

Primary Examiner—Patrick P. Garvin
Assistant Examiner—E. D. Irzmeh
Attorney, Agent, or Firm—Cushman, Darby & Cushman

[57] ABSTRACT

Process for preparing an alkyl substituted tetralin or indane by reacting a benzyl alcohol with an alkene having 4–7 carbon atoms under the influence of a Lewis acid catalyst. The product can be further reacted with an acyl halide or alkylene epoxide without prior isolated from the initial reaction mixture.

12 Claims, No Drawings

PROCESS FOR THE PREPARATION OF ALKYL SUBSTITUTED TETRALINS AND INDANES

This application is a continuation-in-part of Ser. No. 07/508,716, filed Apr. 16, 1990, now abandoned.

The invention relates to a process for the preparation of alkyl substituted tetralins and indanes.

Alkyl substituted tetralins and indanes are important in the fragrance industry as intermediates for the preparation of well known musk fragrances of the acetylated tetralin, acetylated indane and the isochroman type. Many routes have therefore been developed to synthesize these intermediates and the majority of these routes are focused on the preparation of a benzylic cation to react with a suitable alkene followed by ring closure. These cations have been prepared either from the corresponding hydrocarbon by hydride abstraction, from a suitably substituted styrene by protonation of from a benzyl halide by halide abstraction. Many of these routes were reviewed in: T. F. Wood, the chemistry of the Aromatic Musks, edited by Givaudan Corporation, Clifton, N.J., especially pages 10–29. More recent examples are given in U.S. Pat. No. 3,856,875, JP-A-54/125647 (1979), JP-A-56/043221 (1981), JP-A-56/039026 (1981) and EP-A-089207. However, there is a need for a process which gives higher yields and/or uses cheaper starting materials.

A process was found for the preparation of alkyl substituted tetralins and indanes using a tertiary benzyl alcohol having formula I:

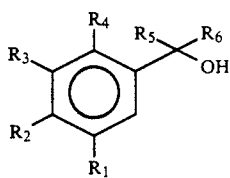

FORMULA I wherein $R_1$–$R_4$ represent hydrogen atoms or alkyl groups having 1–3 carbon atoms and $R_5$ and $R_6$ are alkyl groups having 1–3 carbon atoms, which is reacted with an alkene having 4–7 carbon atoms under the influence of a Lewis acid catalyst whereby a tetralin having formula II and/or an indane having formula III is obtained:

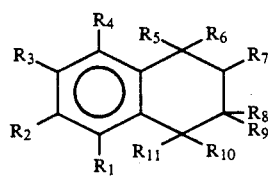

FORMULA II

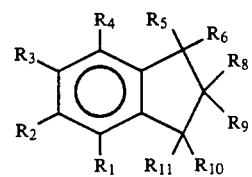

FORMULA III wherein $R_1$–$R_6$ have the meaning indicated above and $R_7$–$R_{11}$ represent hydrogen atoms or alkyl groups having 1–4 carbon atoms, with the proviso that the total number of carbon atoms in $R_7$–$R_{11}$ does not exceed 4 in formula II or in $R_8$–$R_{11}$ does not exceed 5 in formula III.

In G. A. Olah, "Friedel-Crafts and Related Reactions", Vol. II, Part 2; Interscience Publishers, N.Y., 1964, pp. 816–822 it is disclosed that unlike other phenyl-substituted alkanols, 1-phenyl-alkan-1-ols (alpha-alkyl-substituted benzyl alcohols) do not react with strong acids to yield tetralin- or indane-type products, but instead give intractable polymers. A passing reference to the reaction of 2-methyl-1-(p-methylphenyl)-propan-1-ol, which is a secondary benzyl alcohol, with 2-methylbut-2-ene or 2,3-dimethyl-2-ene to obtain the corresponding 1-isopropyl-indane was made in U.S. Pat. No. 4,352,748, however without giving any further details. The at first sight more cumbersome route of first converting the alcohol into the corresponding chloride before reaction with the alkene is given in Example 1 of this patent and is apparently preferred.

The process according to the present invention generally provides the substituted tetralins or indanes in high yield starting from relatively cheap and easily available benzyl alcohols. These alcohols are the starting materials for the preparation of the styrene or benzyl chloride substrates used in prior art processes for preparing the tetralins and indanes. Thus the process according to the invention provides an appreciable simplification of the reaction route leading to these products.

The preferred benzyl alcohols according to formula I are those wherein $R_1$, $R_3$ and $R_4$ are hydrogen atoms and $R_2$ is either a hydrogen atom or a methyl group. Especially preferred are benzyl alcohols wherein also $R_5$ and $R_6$ are both methyl groups. Preferred alkenes for the process according to the invention are 2,3-dimethylbut-1-ene, 3,3-dimethylbut-1-ene and 2-methylbut-2-ene. These alkenes will lead to tetralins of formula II wherein $R_7$ and $R_8$ are both hydrogen atoms and $R_9$–$R_{11}$ are all methyl groups or indanes of formula III wherein $R_8$ is a hydrogen atom and $R_9$–$R_{11}$ are all methyl groups. Alternatively the reaction with the above mentioned dimethylbutenes may be so directed, e.g. as described in U.S. Pat. No. 4,493,790 as to produce predominantly the indane of formula III wherein $R_8$ and $R_9$ are hydrogen atoms, $R_{10}$ is a methyl group and $R_{11}$ is an isopropyl group. Instead of pure alkenes, commercially available alkene mixtures which are rich in one or more of the above mentioned alkenes are also very suitably for the purposes of the invention.

The usual Lewis acid catalysts may be used for the reaction according to the invention. Particularly suitable are $AlCl_3$, $FeCl_3$ and $TiCl_4$. Optionally, known complexing agents, such as nitroalkanes, may be used, especially in combination with $AlCl_3$. The catalyst is used in an amount of at least 0.1 mol, and preferably between 0.5 and 1.0 mol per mol of benzyl alcohol. Equimolar amounts of alkene and benzyl alcohol or even an excess of the alcohol may be used, however the use of an excess of alkene is preferred. A molar ratio of alkene/alcohol of 1:1 to 5:1 is very suitable.

The usual solvents for Friedel-Crafts alkylation reactions may be used, e.g. aromatic hydrocarbons such as toluene, o-, m- or p-xylene, o-, m- or p-cymene, aliphatic hydrocarbons, such as dichloromethane, 1,1- and 1,2-dichloroethane, 1,1,1-trichloroethane, tetrachloroethylene and carbon tetrachloride, nitro-alkanes, such as nitromethane, nitroethane and nitropropane, liquid sulphur dioxide and sulpholane and mixtures of such solvents. Aromatic and aliphatic hydrocarbons are the preferred solvents, if for environmental reasons a non-chlorinated solvent should be used. Preferably a minimum volume of 150 ml of solvent per mol of alcohol is used. The temperature at which the reaction is carried out is not critical, although temperatures below ambient tend to increase the selectivity of the reaction. Temperatures between −80° and +80° C. and preferably between −30° and +10° C., but above the freezing point of the solvent, are generally suitable. It is recommended that the reaction be carried out in the absence of water and oxygen.

The tetralins and indanes provided by the process according to the invention are highly suitable for the preparation of well known musk fragrances. This preparation often involves acylation of said tetralins and indanes with an acyl halide, more particularly an acetylation with acetyl halide, also under the influence of a Lewis acid catalyst. Furthermore, the tetralins and indanes may be reacted with a suitable alkylene epoxide, especially propylene oxide, to form precursors for iso-chroman compounds. All the aforesaid reactions may be carried out after isolation of the tetralin or indane from the initial reaction mixture. However, they may also be carried out without such prior isolation. Thus, the process according to the invention also comprises a further reaction with an acyl halide or an epoxide, using if necessary additional Lewis acid catalyst, without prior isolation of the tetralin or indane from the initial reaction mixture.

The following examples illustrate how to perform the process according to the invention. However, the invention is not limited thereto.

EXAMPLE 1

To a stirred solution of 10 ml titanium tetrachloride in 120 ml dichloromethane which had been cooled to −5° C. under nitrogen, was added a mixture of 15.0 g (0.1 mol) p-cymen-8-ol and 16.8 g (0.2 mol) 2,3-dimethylbut-1-ene over a two hour period. The reaction mixture was stirred for a further 30 minutes at −5° C. Thereafter it was poured into a mixture of 200 ml water and 100 ml of concentrated hydrochloric acid and stirred for 15 minutes. The organic phase was separated and the aqueous phase washed twice with 50 ml dichloromethane. The combined organic phase was washed twice with 100 ml 10% hydrochloric acid solution, once with 100 ml water twice with 100 ml 5% sodium carbonate solution and finally once again with water. After removal of the solvent 25.3 g of a crude reaction product was obtained, containing 71.1% (17.9 g) of the desired 1,1,3,4,4,6-hexamethyltetralin, equivalent to a 83.3% yield based on p-cymenol used. The hexamethyltetralin was purified by crystallisation from an equal weight of iso-propanol; m.p. 66°-67° C. The reaction was repeated and the crude hexamethyltetralin thus produced was purified by fractional distillation under reduced pressure; b.p. 98°-102° C./0.7 kPa.

EXAMPLE 2

The procedure of Example 1 was repeated except that the solvent used was cyclohexane instead of dichloromethane. The yield of hexamethyltetralin was 66.4% based on p-cymen-8-ol.

EXAMPLE 3

A mixture of 66.8 g of aluminium chloride and 400 ml of dichloromethane was cooled to −10° C. and kept under nitrogen. A mixture of 75 g (0.5 mol) p-cymen-8-ol and 63 g (0.75 mol) 2,3-dimethylbut-1-ene was added over a two hour period while maintaining the temperature of the reaction mixture at −10° C. The mixture was stirred at this temperature for another 30 minutes, poured into 1200 ml of a 10% aqueous solution of hydrochloric acid and further worked up as in Example 1. The desired hexamethyltetralin was obtained in 35.3% yield based on p-cymenol.

EXAMPLE 4

A mixture of 6.7 g aluminium chloride and 30 ml dichloromethane was cooled to −5° C. and 5.6 g of nitroethane added. Thereafter a mixture of 7.6 g p-cymen-8-ol and 8.4 g 2,3-dimethylbut-1-ene was added over a period of 35 minutes, while keeping the temperature at −5° C. After stirring at this temperature for another 10 minutes the reaction mixture was worked up at in Example 1. The yield of hexamethyltetralin was 69% based on p-cymenol.

EXAMPLE 5

The procedure of Example 4 was repeated except that the reaction was carried out using 30 ml of nitroethane alone as the solvent. the yield of the desired tetralin was 90% based on p-cymenol.

EXAMPLE 6

To 60 ml of 1,2-dichloroethane, cooled to −10° C. and kept under nitrogen, was gradually added whilst stirring a mixture of 30 g p-cymen-8-ol and 26 g 2,3-dimethylbut-1-ene over a period of 90 minutes. Separately, but simultaneously, a mixture of 10 ml titanium tetrachloride and 40 ml 1,2-dichloroethane was added over a period of 80 minutes. The reaction temperature was kept at −10° C. during the addition of the reagents and thereafter for 30 minutes whilst stirring. The reaction mixture was worked up as described in Example 1. The yield of tetralin was 81.4% of the theoretical.

EXAMPLE 7 p-Cymene (500 ml) was charged into a 2 liter reaction vessel equipped with a stirrer, a thermometer, a nitrogen inlet, a reflux condensor and two additional ports. The solvent was cooled to −20° C. and thereafter a mixture of 150 g p-cymenol and 130 g 2,3-dimethylbut-1-ene was added through one port and simultaneously 55 ml titanium tetrachloride was added through the other port while stirring. The flows were regulated such that both additions took 1.5 hours. During the additions, the temperature of the reaction mixture was maintained at −20° C. After the addition, the reaction mixture was stirred for another 10 minutes, quenched into 500 ml of water and the resulting mixture stirred for 30 minutes. The organic phase was separated and washed successively with 10% v/v hydrochloric acid solution (200 ml), 10% w/w sodium hydroxide solution (200 ml) and water (300 ml). The solvent was removed by distillation to yield a crude product comprising 146 g 1,1,3,4,4,6-hexamethyltetralin (71.9% yield) in addition to 42.9 g 3-isopropyl-1,1,3,5-tetramethylindane and some minor products. The crude mixture was further purified by fractional distillation as described in example 1.

We claim:

1. Process for the preparation of alkyl substituted tetralins and indans characterized in that a benzyl alcohol having formula I:

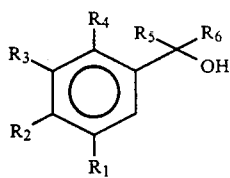

FORMULA I wherein $R_1$–$R_4$ represent hydrogen atoms or alkyl groups having 1–3 carbon atoms and $R_5$ and $R_6$ are alkyl groups having 1–3 carbon atoms, is reacted with an alkene having 4–7 carbon atoms under the influence of a Lewis acid catalyst.

2. Process according to claim 1 wherein a benzyl alcohol is used, having formula I wherein $R_1$, $R_3$ and $R_4$ are hydrogen atoms and $R_2$ is a hydrogen atom or a methyl group.

3. Process according to claim 2 wherein the alkene is chosen from 2,3-dimethylbut-1-ene, 3,3-dimethyl-1-ene and 2-methyl-but-2-ene.

4. Process according to claim 3 wherein a benzyl alcohol is used, having formula I wherein $R_5$ and $R_6$ are both methyl groups.

5. Process according to claim 1 wherein the Lewis acid is chosen from $AlCl_3$, $FeCl_3$ and $TiCl_4$.

6. Process according to claim 5 wherein a complexing agent is added to the reaction mixture.

7. Process according to claim 6 wherein the complexing agent is a nitroalkane.

8. Processing according to claim 1 wherein the tetralin or the indane obtained is further reacted with an acyl halide or an alkylene epoxide under the influence of a Lewis acid catalyst, without prior isolation from the initial reaction mixture.

9. Process according to claim 8 wherein the acyl halide is acetyl halide.

10. Process according to claim 8 wherein the alkylene epoxide is propylene epoxide.

11. Process according to claim 8 wherein an additional amount of Lewis acid chosen from $AlCl_3$, $FeCl_3$ and $TiCl_4$ is added between the alkylation step and the reaction with the acylhalide or alkylene epoxide.

12. Process according to claim 1 wherein the alkene is chosen from 2,3-dimethylbut-1-ene, 3,3-dimethylbut-1-ene and 2-methyl-but-2-ene, the Lewis acid is chosen from $AlCl_3$, $FeCl_3$ and $TiCl_4$ and an aromatic or aliphatic hydrocarbon is used as the solvent.

* * * * *

UNITED STATES PATENT AND TRADEMARK OFFICE
CERTIFICATE OF CORRECTION

PATENT NO. : 5,079,386
DATED : January 7, 1992
INVENTOR(S) : Meakins et al It is certified that error appears in the above-identified patent and that said Letters Patent is hereby corrected as shown below:

Column 2, line 63, "hydrocarbons," should be --hydrocarbons, such as hexane and cyclohexane, chlorinated hydrocarbons,--.

Column 4, line 18, "at" should be --as--.

Signed and Sealed this

Twenty-fifth Day of May, 1993

Attest:

MICHAEL K. KIRK

*Attesting Officer*   *Acting Commissioner of Patents and Trademarks*